US012232779B2

(12) United States Patent
Shin

(10) Patent No.: US 12,232,779 B2
(45) Date of Patent: Feb. 25, 2025

(54) SURGICAL INSTRUMENT

(71) Applicant: Sung Joon Shin, Incheon (KR)

(72) Inventor: Sung Joon Shin, Incheon (KR)

( * ) Notice: Subject to any disclaimer, the term of this patent is extended or adjusted under 35 U.S.C. 154(b) by 175 days.

(21) Appl. No.: 17/793,779

(22) PCT Filed: Jan. 19, 2021

(86) PCT No.: PCT/KR2021/000753
§ 371 (c)(1),
(2) Date: Jul. 19, 2022

(87) PCT Pub. No.: WO2021/150001
PCT Pub. Date: Jul. 29, 2021

(65) Prior Publication Data
US 2023/0058978 A1    Feb. 23, 2023

(30) Foreign Application Priority Data

Jan. 20, 2020 (KR) .................. 10-2020-0007041

(51) Int. Cl.
*A61B 17/70* (2006.01)
*A61B 17/00* (2006.01)
(52) U.S. Cl.
CPC ...... *A61B 17/7062* (2013.01); *A61B 17/7064* (2013.01); *A61B 2017/00314* (2013.01)
(58) Field of Classification Search
CPC ................ A61B 17/7062; A61F 2/4611
See application file for complete search history.

(56) References Cited

U.S. PATENT DOCUMENTS

| 9,498,264 B2 * | 11/2016 | Harshman ........ A61B 17/7283 |
| 2013/0053868 A1 | 2/2013 | Cooper et al. |
| 2013/0199327 A1 * | 8/2013 | Park .................. F16C 11/04 |
| | | 403/121 |
| 2017/0095922 A1 * | 4/2017 | Licht ................ A61B 34/71 |
| 2018/0200895 A1 * | 7/2018 | Kan .................. A61B 34/30 |

FOREIGN PATENT DOCUMENTS

| JP | 2010-036039 A | 2/2010 |
| JP | 2018-531694 A | 11/2018 |
| KR | 100995776 B1 * | 11/2010 | ............ A61B 17/29 |
| KR | 10-2013-0090623 A | 8/2013 |
| KR | 10-1647453 B | 8/2016 |
| KR | 10-2019-0112195 A | 10/2019 |
| WO | 2012-166499 A1 | 12/2012 |

OTHER PUBLICATIONS

English-language translation of description of KR-100995776-B1; provided by espacenet.com; accessed on Mar. 8, 2024.*

* cited by examiner

*Primary Examiner* — Julianna N Harvey
(74) *Attorney, Agent, or Firm* — INVENSTONE PATENT, LLC

(57) ABSTRACT

Disclosed is an apparatus for operation that can be inserted into an incision hole in spinal endoscopic surgery. An apparatus for operation includes a rod, a rotating part rotatably connected to the rod, and a bending part connected to the rotating part and bendable, in which the bending part includes a plurality of links being in rolling contact with each other, and a plurality of wires connecting the plurality of links.

11 Claims, 9 Drawing Sheets

SURGICAL INSTRUMENT

CROSS-REFERENCE TO RELATED APPLICATIONS

This application is a National Stage filing under 35 U.S.C. 371 of International Application No. PCT/KR2021/000753, filed on Jan. 19, 2021, which claims the benefit of earlier filing date and right of priority to Korean Application No. 10-2020-0007041, filed on Jan. 20, 2020, in the Korean Intellectual Property Office, the contents of which are all hereby incorporated by reference herein in their entirety.

BACKGROUND OF THE DISCLOSURE

Technical Field

The present invention relates to an apparatus for operation, and more particularly, to an apparatus for operation for spinal surgery.

Background Art

In order to solve instability of a vertebral segment after disc resection or posterior decompression surgery, interspinous spacer insertion, which inserts an interspinous spacer between patient's spinous processes, is being performed.

The interspinous spacer insertion includes a process of incising a certain section of a site to be operated, inserting a spacer between spinous processes adjacent to each other through an incised site, and wrapping around the spinous processes using a strap, a band, or the like to fix the spacer between adjacent spinous processes.

A tension band insertion apparatus is used as an apparatus for wrapping around the spinous process with the strap or the band.

As illustrated in FIG. 1, a tension band insertion device 1 has a bent shape so that an end portion of the tension band insertion mechanism 1 wraps around a spinous process S. A hole 3 is formed in the tension band insertion mechanism 1, and the strap 5 is inserted into the hole 3.

As an end of the tension band insertion device 1 is rotated or moves along a circumference of a patient's spinous process, the strap 5 wraps around the spinous process.

Recently, even in the interspinous spacer insertion, instead of incising a site to be operated as much as a certain section, methods of forming several incision holes around the site to be operated, and inserting an endoscope and apparatuses for operation through the incision holes to fix the interspinous spacer have been attempted.

However, in the case of the tension band insertion mechanism 1 illustrated in FIG. 1, there is a problem that does not pass through the incision hole due to the shape bent to wrap around the spinous process.

(Patent Document 1) Korean Patent No. 10-1647453

SUMMARY OF THE DISCLOSURE

The present invention provides an apparatus for operation that can be inserted through an incision hole in spinal endoscopic surgery.

Aspects of the present invention are not limited to the above-described aspects. That is, other aspects that are not described may be obviously understood by those skilled in the art from the following specification.

According to an aspect of the present invention, an apparatus for operation inserted into a body through an incision hole may include: a rod; a rotating part rotatably connected to the rod; and a bending part connected to the rotating part and bendable, in which the bending part may include: a plurality of links being in rolling contact with each other; and a plurality of wires connecting the plurality of links.

The plurality of wires may include: a switching wire configured to bring the plurality of links into contact with each other or space the plurality of links from each other; and an adjustment wire configured to bend the bending part while the plurality of links is spaced apart from each other.

The rod may include: a first driving adjustment unit configured to adjust rotation of the rotating part; and a second driving adjustment unit configured to adjust a tension applied to the plurality of adjustment wires.

The apparatus for operation may further include: a first driving force transmission unit configured to be disposed between the first driving adjustment unit and the rotating part, in which the rotating part may be rotated by receiving power by the first driving adjustment unit through the first driving force transmission unit.

The apparatus for operation may further include: a second driving force transmission unit configured to be disposed between the second driving adjustment unit and the bending part, in which the bending part may include a driving plate rotated by receiving power by the second driving adjustment unit through the second driving force transmission unit.

A portion of the plurality of adjustment wires may be configured to be wound around an outer circumferential surface of the driving plate.

The apparatus for operation may be configured to have a first shape in which the rotating part and the bending part are arranged substantially parallel to the rod so that the rotating part and the bending part are inserted into the body through the incision hole, and a second shape in which the rotating part is rotated with respect to the rod or the bending part is bent so that the bending part wraps around a spinous process in the body.

The link may include a link body, a convex portion formed on one side of the link body, and a concave portion formed on the other side of the link body, and the concave portion may be provided with a plurality of elastic bodies.

The apparatus for operation may further include: a blade configured to be coupled to a last link among the plurality of links and receive a current.

The link may include a plurality of first through holes formed at an edge of the link body and a second through hole formed at a center of the link body, and each of the plurality of adjustment wires may extend through the plurality of first through holes, and the switching wire may extend through the second through holes.

The plurality of first through holes may be disposed on an outer side of the concave portion along a radial direction of the link.

The blade may be inserted into the second through hole and connected to the switching wire.

The bending part may be configured so that at least a portion of the bending part is supplied with a current.

According to another aspect of the present invention, an apparatus for operation inserted into a body through an incision hole may include: a plurality of links in rolling contact with each other; and a bending part having a plurality of wires connecting the plurality of links; and a guide part having a hollow body provided therein so that the bending part is inserted and guided, and a wrinkle part connected to one end of the body and provided in a rotatable form.

According to still another aspect of the present invention, an apparatus for operation inserted into a body through an incision hole may include: a rod; and a bending part connected to the rod and bendable, in which the bending part may include: a plurality of links being in rolling contact with each other; and a plurality of wires connecting the plurality of links.

According to an exemplary embodiment of the present invention, an apparatus for operation is provided to have a shape that can pass through an incision hole.

In addition, after an apparatus for operation is inserted into a body through an incision hole, a shape of the apparatus may be deformed to be suitable for surgery, so surgery may be performed through an incision hole instead of incising a certain section of a site to be operated.

DETAILED DESCRIPTION OF THE DISCLOSURE

Figure 1:
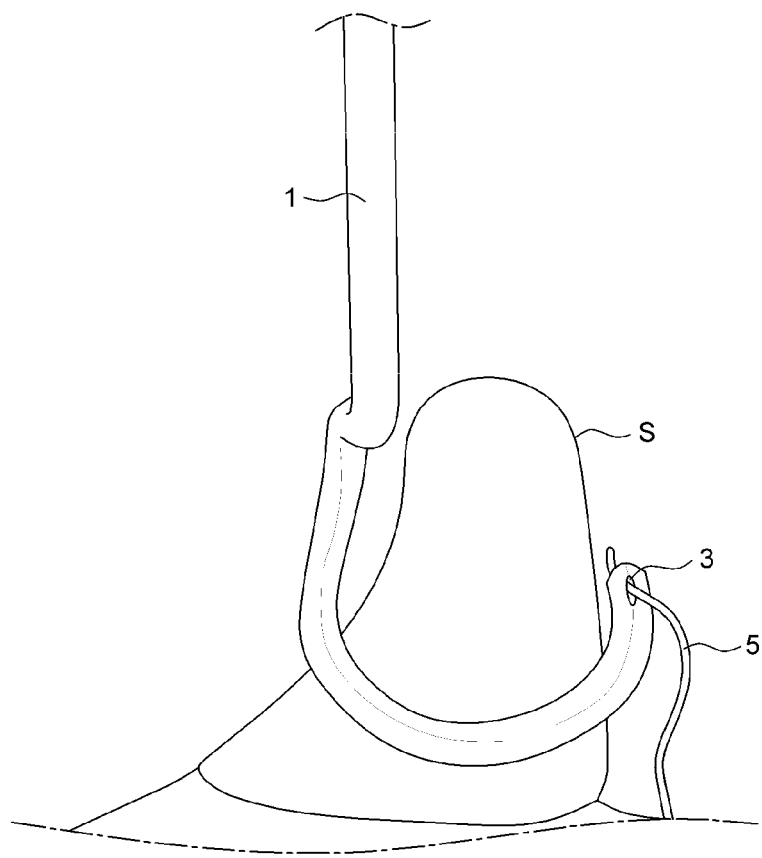
FIG. 1 is a diagram schematically illustrating a conventional apparatus for operation.

Hereinafter, various exemplary embodiments will be described in more detail with reference to the accompanying drawings. Exemplary embodiments described in the present specification may be variously modified. A specific exemplary embodiment may be illustrated in the drawings and be described in detail in a detailed description. However, the specific exemplary embodiment illustrated in the accompanying drawings is provided only to allow various exemplary embodiments to be easily understood. Therefore, it should be understood that the spirit of the present invention is not limited by the specific exemplary embodiment illustrated in the accompanying drawings, but includes all the modifications, equivalents, and substitutions included in the spirit and the scope of the present invention.

Terms including ordinal numbers such as "first", "second", and the like, may be used to describe various components. However, these components are not limited by these terms. The terms are used only to distinguish one component from another component.

It should be further understood that terms "include" or "have" used in the present specification specify the presence of features, numerals, steps, operations, components, parts described in the present specification, or combinations thereof, but do not preclude the presence or addition of one or more other features, numerals, steps, operations, components, parts, or combinations thereof. It is to be understood that when one element is referred to as being "connected to" or "coupled to" another element, it may be connected directly to or coupled directly to another element or be connected to or coupled to another element, having the other element intervening therebetween. On the other hand, it should be understood that when one element is referred to as being "connected directly to" or "coupled directly to" another element, it may be connected to or coupled to another element without the other element interposed therebetween.

Meanwhile, a term "module" or "~er/~or" for components used in the present specification performs at least one function or operation. In addition, a "module" or a "~er/~or" may perform a function or an operation by hardware, software, or a combination of hardware and software. In addition, a plurality of "modules" or a plurality of "~ers/~ors" except for a "module" or a "~er/~or" performed by specific hardware or performed by at least one processor may be integrated into at least one module. Singular forms are intended to include plural forms unless the context clearly indicates otherwise.

Further, when it is decided that a detailed description for the known function or configuration related to the present invention may obscure the gist of the present invention, the detailed description therefor will be abbreviated or omitted.

Figure 2:
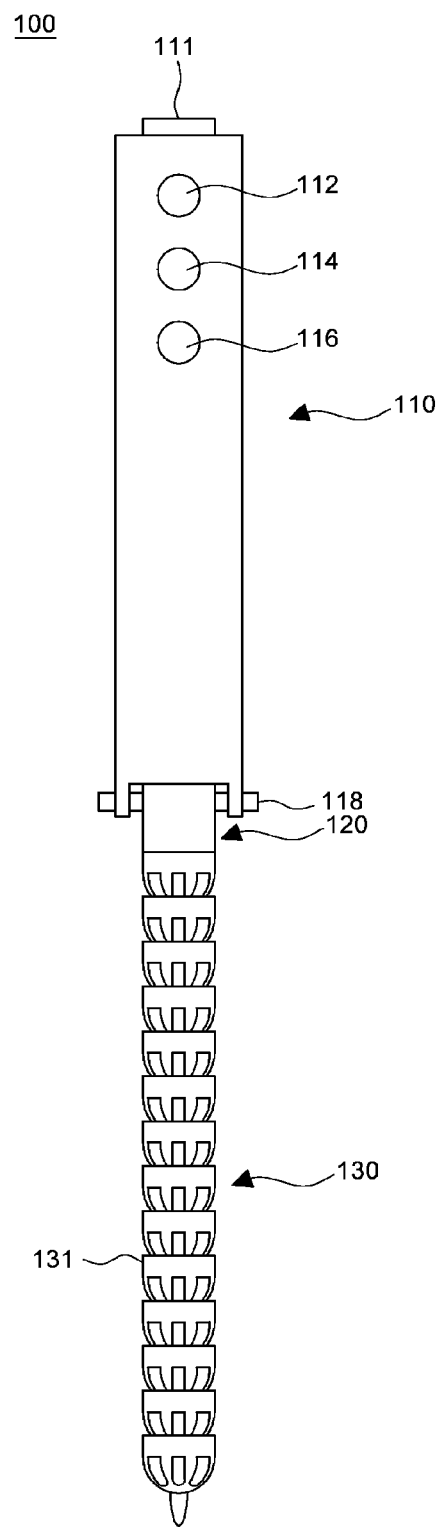
FIG. 2 is a diagram schematically illustrating an apparatus for operation according to an exemplary embodiment of the present invention.
Figure 3:
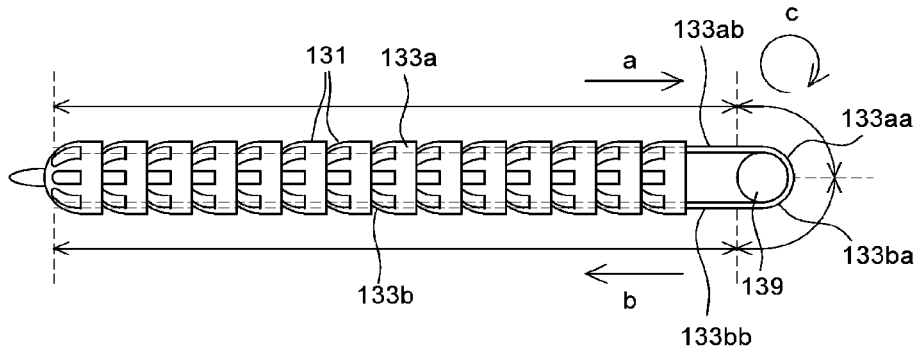
FIG. 3 is a diagram illustrating a bending part.

FIG. 2 is a diagram schematically illustrating an apparatus for operation according to an exemplary embodiment of the present invention, and FIG. 3 is a diagram illustrating a bending part.

Referring to FIG. 2, an apparatus 100 for operation according to an exemplary embodiment of the present invention includes a rod 110, a rotating part 120, and a bending part 130.

The rod 110, the rotating part 120, and the bending part 130 are metal or plastic, such as stainless steel, and in addition, may include various materials that have strong corrosion resistance and are harmless to the human body.

The rod 110 is provided in a cylindrical shape having an accommodation space therein. A first driving force transmission unit and a second driving force transmission unit to be described later may be disposed in the accommodation space.

The rotating part 120 is rotatably connected to one end of the rod 110. One end of the rod 110 may be provided with a shaft 118, and the rotating part 120 may be rotatably coupled to the shaft 118.

The rod 110 includes a first driving adjustment unit 111 for driving the rotating part 120.

The first driving adjustment unit 111 may be rotatably connected to the rod 110. Although not illustrated, the first driving adjustment unit 111 may be connected to the rod 110 in the form of a button. A first driving force transmission unit (not illustrated) is disposed between the first driving adjustment unit 111 and the rotating part 120. The first driving force transmission unit includes power transmission elements (not illustrated) for connecting the first driving adjustment unit 111 and the rotating part 120. The power transmission elements may include gears, belts, cams, wires, etc., used to transmit power, and combinations thereof.

In a structure in which the first driving adjustment unit 111 is rotatably connected to the rod 110, when the first driving adjustment unit 111 is rotated, the rotating part 120 is rotated through the first driving force transmission unit. A rotation amount (angle) of the rotating part 120 is determined according to a rotation angle of the first driving adjustment unit 111, so the rotation angle of the first driving adjustment unit 111 may be adjusted by adjusting the rotation amount (angle) of the rotating part 120.

In the structure in which the first driving adjustment unit 111 is connected to the rod 110 in the form of a button, when the first driving adjustment unit 111 is pressed, the rotating part 120 is rotated through the first driving force transmission unit, so the rotation amount (angle) of the rotating part 120 may be adjusted through a process of pressurizing the first driving adjustment unit 111 or releasing a pressure applied to the first driving adjustment unit 111.

In addition, although not illustrated, a structure in which the rotation angle of the rotating part 120 is adjusted by a rotation of a fully automatic motor (not illustrated) in a button type is also applicable.

When the rotating part 120 is rotated to a desired position, the rotating part 120 may be fixed to the rotated position by a locking device (not illustrated) or the like.

The bending part 130 is bendably connected to the rotating part 120. The bending part 130 includes a plurality of links 131, a plurality of adjustment wires 133, and a switching wire 135.

The plurality of links 131 may be in rolling contact with each other. Hereinafter, the link structure and connection relationship will be described in detail.

Figure 4:
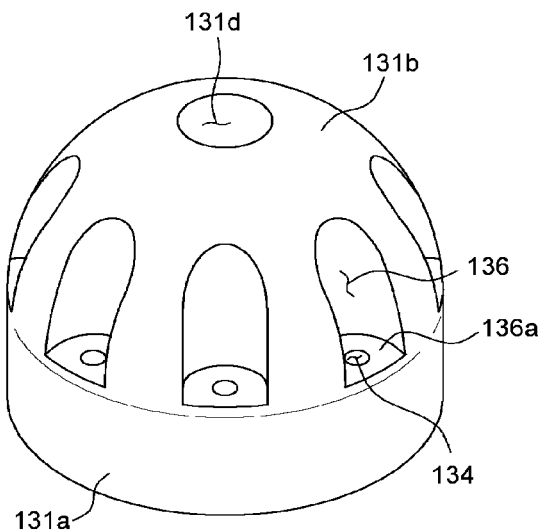
FIG. 4 is a diagram illustrating a link constituting the bending part.
Figure 5:
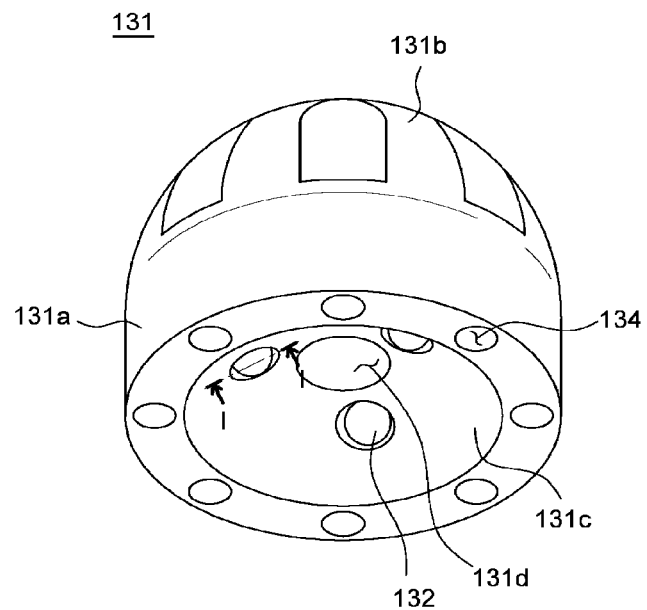
FIG. 5 is a diagram illustrating a lower portion of a link illustrated in FIG. 4.
Figure 6:
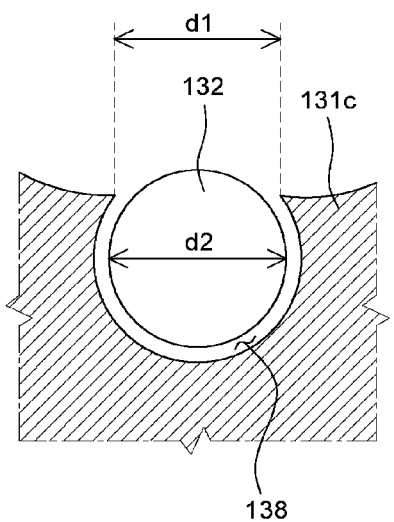
FIG. 6 is a cross-sectional view taken along line I-I' of FIG. 5.
Figure 7:
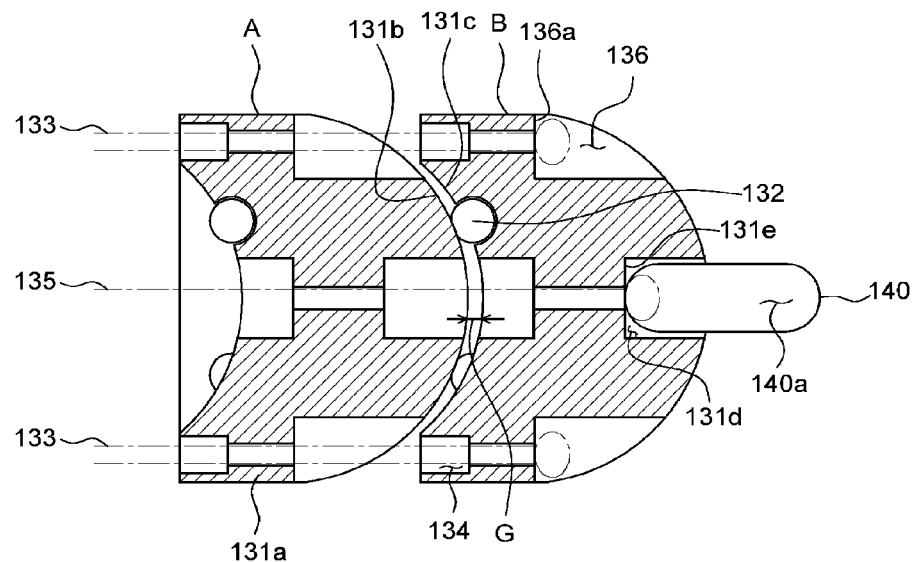
FIG. 7 is a diagram illustrating a state in which adjacent links may move relative to each other.
Figure 8:
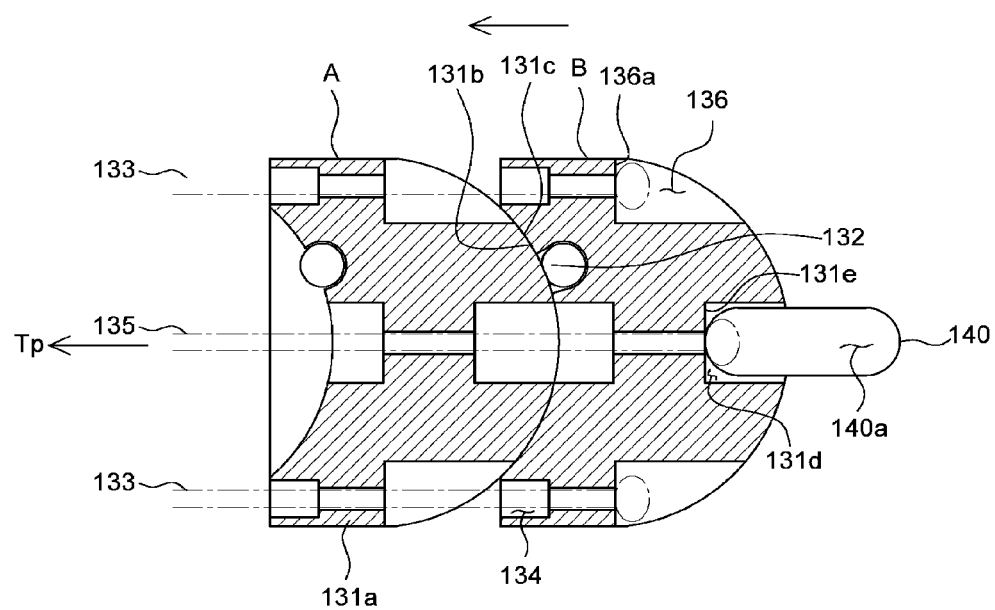
FIG. 8 is a diagram illustrating a state in which adjacent links are fixed to each other.

FIG. 4 is a diagram illustrating a link constituting the bending part, FIG. 5 is a diagram illustrating a lower portion of the link illustrated in FIG. 4. FIG. 6 is a cross-sectional view taken along line I-I of FIG. 5, FIG. 7 is a diagram illustrating a state in which adjacent links may move relative to each other, and FIG. 8 is a diagram illustrating a state in which adjacent links are fixed to each other.

As illustrated in FIGS. 4 and 5, the link 131 includes a link body 131*a*, a convex portion 131*b* formed on one side of the link body 131*a*, and a concave portion 131*c* formed on the other side of the link body 131*a*.

The convex portion 131*b* is formed in a hemispherical shape, and the concave portion 131*c* is formed in a shape corresponding to the convex portion 131*b*. Although not illustrated, the convex portion 131*b* may have an elliptical shape other than a hemispherical shape or other shapes capable of relative rotation with other concave portions 131*c*, or may have a joint-type structure.

A plurality of first through holes 134 is formed at an edge of the link 131. The plurality of first through holes 134 is disposed on an outer side of the concave portion 131*c* in the radial direction of the link 131.

The plurality of first through holes 134 is spaced apart from each other in a circumferential direction of the link 131. The plurality of adjustment wires 133 each passes through the corresponding first through hole 134 to connect the plurality of links 131.

A plurality of guide grooves 136 is formed in a portion corresponding to the first through hole 134 of the convex portion 131*b* to allow the adjustment wires 133 to pass therethrough. The plurality of guide grooves 136 is provided in the number corresponding to the first through hole 134. The plurality of guide grooves 136 is formed at positions corresponding to the first through holes 134 and is spaced apart from each other in the circumferential direction of the link 131.

The link 131 includes a plurality of first locking protrusions 136*a* formed at positions corresponding to the plurality of guide grooves 136. The adjustment wires 133 may be fixed by being caught on the first locking protrusions 136*a* of the link 131 located at the most distal end, respectively.

A plurality of elastic bodies 132 is disposed in the concave portion 131*c* along the circumferential direction of the link body 131*a*. The elastic body 132 is provided in a spherical shape, and is rotatably disposed in the concave portion 131*c*, and at least a portion of the elastic body 132 protrudes from the concave portion 131*c*. Although not illustrated, in addition to the elastic body, a rigid body having an appropriate frictional force on the surface is also applicable. For example, a rigid body having a metallic spherical shape may be applied instead of the elastic body 132.

When an external force is applied to the elastic body 132, the shape of the elastic body 132 is deformed and inserted into the concave portion 131*c*.

The link 131 further includes a second through hole 131*d* formed through the center thereof. The switching wire 135 extends through the second through hole 131*d*.

The link 131 includes a second locking protrusion 131*e* (refer to FIG. 7) formed at a position corresponding to the second through hole 131*d*. The switching wire 135 may be fixed by being caught on a second locking protrusion 131*e* of the link 131 located at the most distal end.

As illustrated in FIG. 6, a plurality of accommodation grooves 138 may be formed in the concave portion 131*c* of the link 131 to accommodate the elastic body 132.

A plurality of elastic bodies 132 is disposed in the plurality of accommodation grooves 138, respectively. The plurality of elastic bodies 132 may be rotated while being accommodated in the plurality of accommodation grooves 138, respectively, and at least a portion of the plurality of elastic bodies 132 may protrude toward the outer side of the concave portion 131*c*.

A diameter d1 of an inlet portion of the accommodation groove 138 may be smaller than a diameter d2 of the elastic body 132. Therefore, the spherical elastic body 132 accommodated in the accommodation groove 138 may not be separated from the accommodation groove 138. Also, the spherical elastic body 132 may be inserted into the accommodation groove 138 through the inlet portion 138*a* of the accommodation groove 138 while its volume is reduced due to its own elasticity.

As illustrated in FIGS. 7 and 8, the plurality of links 131 constituting the bending part 130 is disposed to be in contact with each other. For convenience of explanation, two links disposed at the distal ends of the bending part 130 are illustrated in FIGS. 7 and 8, and will be collectively referred to as a first link A and a second link B, respectively. That is, both the first link A and the second link B are included in the plurality of links 131 constituting the bending part 130, and the second link B is a link located at the most distal end of the bending part 130.

As illustrated in FIG. 7, in a state (hereinafter, referred to as bending mode) in which adjacent links may move relative to each other, the convex portion 131*b* of the first link A is spaced apart from the concave portion 131*c* of the second link B by a predetermined distance G. In addition, in the bending mode, the convex portion 131*b* of the first link A is disposed so as to be in contact with the elastic body 132 protruding from the concave portion 131c of the second link B.

Accordingly, the first link A and the second link B may move relative to each other, and the bending part 130 may be bent by adjusting the tension of the adjustment wires 133 connecting the plurality of links 131.

A pair of adjustment wires 133 spaced apart from each other 180° in the circumferential direction of the link 131 provide a degree of freedom for bending in two directions. In the present exemplary embodiment, since all four pairs of adjustment wires 133 pass through the links 131 and connect the links 131, the bending part 130 has a degree of freedom for bending in 8 directions. The degree of freedom for bending can be adjusted through the number of adjustment wires 133.

As illustrated in FIG. 8, when a tension Tp is applied to the switching wire 135, the convex portion 131b of the first link A presses the elastic body 132, and the pressed elastic body 132 is compressed to change its shape, and thus, completely inserted into the accommodation groove 138. When the elastic body 132 is completely inserted into the accommodation groove 138, the convex portion 131b of the first link A is into contact with the concave portion 131c of the second link B.

When the first link A and the second link B are in close contact with each other, the frictional force between the convex portion 131b of the first link A and the concave portion 131c of the second link B increases. As a result, the relative motion of the first link A and the second link B is restricted, and the first link A and the second link B are in a fixed state (hereinafter, referred to as a fixed mode). When the tension applied to the switching wire 135 in the fixed mode is released, the first link A and the second link B are switched to the bending mode while being spaced apart from each other, and the bending part 130 may be bent by adjusting the tension of the first wires 133. In this way, in the fixed mode, it is possible to detach muscles around the spinous process and to prevent movement in other directions.

In the case of a structure in which a metallic rigid body (not illustrated) other than the elastic body 132 is inserted into the accommodation groove 138, the relative movement of the first link A and the second link B may be restricted, and the first link A and the second link B may be fixed to each other due to the frictional force between the rigid body and the convex portion 131b of the first link A while the rigid body and the convex portion 131b of the first link A are in contact with each other.

The bending part 130 further includes a driving plate 139 that is rotated by being connected to the second driving force transmission unit to be described later. The driving plate 139 is disposed inside the rotating part 120, and is rotatably connected to the rotating part 120. The driving plate 139 has a circular cross-section. The cross-section of the driving plate 139 may have a polygonal shape other than a circular shape. In addition, the driving plate 139 may have various shapes such as a three-dimensional spherical shape or a polygonal shape.

The adjustment wires 133 are wound and fixed on the outer circumferential surface of the driving plate 139. FIG. 3 illustrates only a pair of adjustment wires 133a and 133b for convenience of explanation.

The pair of adjustment wires 133a and 133b connects the plurality of links 131. The pair of adjustment wires 133a and 133b includes a first wire 133a and a second wire 133b.

The first wire 133a includes a first portion 133aa and a second portion 133ab.

One end of the first portion 133aa of the first wire 133a may be coupled to a portion of the outer circumferential surface of the driving plate 139, and may be wound around the outer circumferential surface of the driving plate 139 or unwound from the outer circumferential surface of the driving plate 139 according to the rotation of the driving plate 139.

The second portion 133ab of the first wire 133a passes through the plurality of links 131 and connects the plurality of links 131. As described above, one end of the second portion 133ab of the first wire 133a is fixed to the second link B disposed at the last among the plurality of links 131.

The second wire 133b includes a first portion 133ba and a second portion 133bb.

One end of the first portion 133ba of the second wire 133b may be coupled to a portion of the outer circumferential surface of the driving plate 139, and may be wound around the outer circumferential surface of the driving plate 139 or unwound from the outer circumferential surface of the driving plate 139 according to the rotation of the driving plate 139.

The second portion 133bb of the second wire 133b passes through the plurality of links 131 and connects the plurality of links 131. As described above, one end of the second portion 133bb of the second wire 133b is fixed to the second link B disposed at the last among the plurality of links 131.

The driving plate 139 described above is one exemplary embodiment for bending the bending part 130, and it is possible to extend the adjustment wires 133 to the rod 110 without the driving plate 139, and it is also possible to bend the bending part 130 by adjusting the tension of the adjustment wires 133 extending to the rod 110.

The rod 110 includes a second driving adjustment unit 112 for driving the bending part 130.

The second driving adjustment unit 112 may be rotatably connected to the rod 110. Although not illustrated, the second driving adjustment unit 112 may be connected to the rod 110 in the form of the button. A second driving force transmission unit (not illustrated) is disposed between the second driving adjustment unit 112 and the bending part 130. The second driving force transmission unit includes power transmission elements (not illustrated) for connecting between the second driving adjustment unit 112 and the bending part 130. The power transmission elements may include gears, belts, cams, wires, etc. used to transmit power, and combinations thereof.

In the structure in which the second driving adjustment unit 112 is rotatably connected to the rod 110, when the second driving adjustment unit 112 is rotated, the bending part 130 may be bent through the second driving force transmission unit. A bending amount (angle) of the bending part 130 is determined according to a rotation angle of the second driving adjustment unit 112, and thus, the bending amount (angle) of the bending part 130 may be adjusted by adjusting the rotation angle of the second driving adjustment unit 112.

In the structure in which the second driving adjustment unit 112 is connected to the rod 110 in the form of the button, when the second driving adjustment unit 111 is pressed, the bending part 130 is bent through the second driving force transmission unit, so the bending amount (angle) of the bending part 130 may be adjusted through a process of pressurizing the second driving adjustment unit 112 or releasing a pressure applied to the second driving adjustment unit 112.

In addition, although not illustrated, a structure in which the rotation angle of the rotating part 120 is adjusted by a rotation of a fully automatic motor (not illustrated) in a button type is also applicable.

When the bending part 130 is bent at a desired position, the bending part 130 may be fixed at the bent position by a locking device (not illustrated) or the like.

In addition, the rod 110 includes a tension adjustment unit 114 for adjusting the tension of the switching wire 135 and a current adjustment unit 116 for supplying a current to the switching wire 135 or adjusting a current flowing in the switching wire 135. The current adjustment unit 116 is electrically connected to a current generator (not illustrated) to be described later.

As illustrated in FIGS. 7 and 8, a blade 140 provided with a hole 140a is coupled to the second link B disposed at the last among the plurality of links 131. The blade 140 may be provided in a polygonal shape with the hole 140a and a spherical shape with the hole 140a, and may be provided in various shapes such as a circular shape, an elliptical shape, and a polyhedron with holes in a two-dimensional plate shape.

The blade 140 is inserted and fixed to the second through hole 131d of the second link B. The blade 140 may include a metal material through which a current may flow.

The blade 140 may be connected to the switching wire 135. The switching wire 135 is configured to receive a current from a current generator or a surgical cauterizer (not illustrated) disposed inside or outside the rod 110. When a current having a specific wavelength and frequency is generated by the current generator (not illustrated), the current is transmitted to the blade 140 through the switching wire 135 to cauterize the tissue around the blade 140 with thermal energy.

In addition to the switching wire 135, the configuration through which the current flows may include all or at least a portion of the adjustment wire 133, the bending part 130, and all or at least a portion of the end link constituting the bending part 130. In this case, all or at least a portion of the adjustment wire 133 and the bending part 130 should be provided with a conductive material such as metal.

The blade 140 is used to remove or deform a portion of soft tissue. Alternatively, the blade 140 may be used to combine tissues, or may be used to cut tissues by replacing a surgical knife or sharp tools.

The intensity of the current applied to the blade 140 may be precisely controlled so as to affect only the tissue of a specific region. This is because the blade 140 is to not only cut tissues by applying force, but also melt a living tissue or cause a living tissue to be stuck by heat generated by a surface contact current. Therefore, through the blade 140, it is possible to easily perform surgery (e.g., detachment of a spinal muscle from a spinous process bone, etc.) and hemostasis even on soft tissue that is difficult to treat.

Although not illustrated, an endoscopic optical fiber, an imaging device (camera), or the like that can be bent to know a site where bleeding occurs during spinal endoscopic surgery and should be required hemostasis can be connected to the bending part 130.

A strap T may be inserted into the hole 140a formed in the blade 140.

Figure 9:
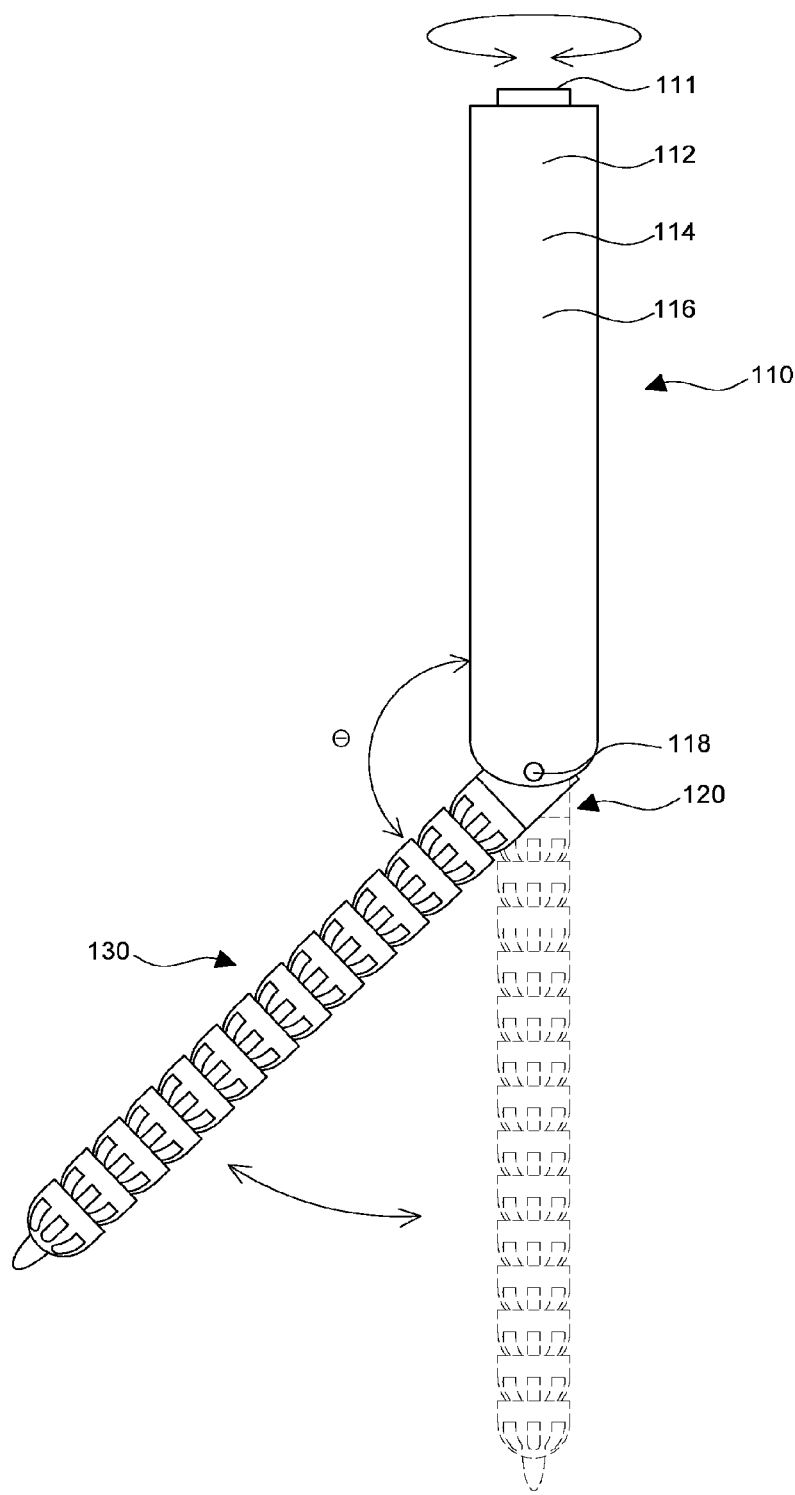
FIG. 9 is a diagram illustrating a state in which a rotating part is rotated.

FIG. 9 is a diagram illustrating a state in which the rotating part is rotated.

Referring to FIG. 9, in a state in which the rod 110, the rotating part 120, and the bending part 130 are aligned in a line, as described above, when the first driving adjustment unit 111 is rotated or pressed to operate, the driving force is transmitted to the rotating part 120 through the first driving force transmission unit.

When power is transmitted to the rotating part 120 through the first driving force transmission unit, the rotating part 120 may be rotated with respect to the shaft 118. When the rotating part 120 is rotated with respect to the axis 118, the rotating part 120 may form an inclination angle θ to the rod 110. The inclination angle θ may have various values depending on various conditions (e.g., surgical environment such as a direction of a patient's incision hole, a shape of the rod, a length of the rod, a position of a patient's spinous process, etc.).

When the rotating part 120 is rotated, the bending part 130 may be rotated together with the rotating part 120.

Figure 10:
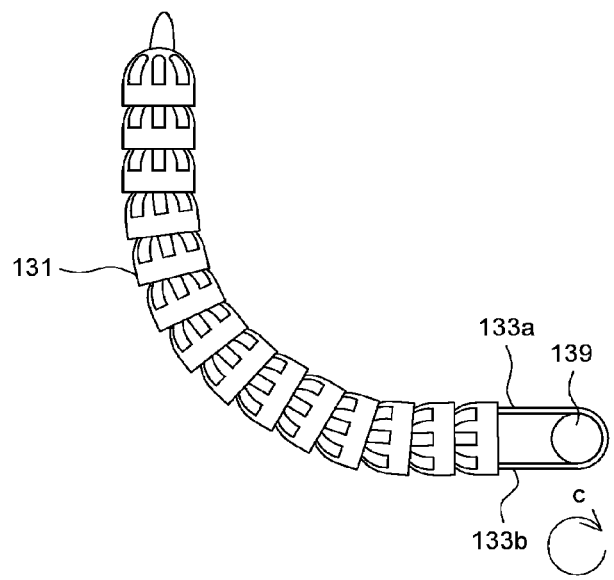
FIG. 10 is a diagram illustrating a state in which the bending part is bent.

FIG. 10 is a diagram illustrating a state in which the bending part is bent.

A process in which the bending part 130 is bent will be described with reference to FIGS. 3 and 9 and 10.

As described above, when the second driving adjustment unit 112 (refer to FIG. 2) is rotated or is pressed to operate, the driving force is transmitted to the driving plate 139 of the bending part 130 through the second driving force transmission unit.

When the driving plate 139 is rotated in a clockwise direction c, the first part 133aa of the first wire 133a and the first part 133ba of the second wire 133b are rotated while the first part 133aa of the first wire 133a and the first part 133ba of the second wire 133b are fixed to a portion of the outer circumferential surface of the driving plate 139. When the first portion 133aa of the first wire 133a and the first portion 133ba of the second wire 133b are rotated in the clockwise direction c, the second portion 133ab of the first wire 133a moves in the first direction a, and the second portion 133bb of the second wire 133b moves in the second direction b opposite to the first direction a.

When the second portion 133ab of the first wire 133a moves in the first direction a, one end of the second portion 133ab of the first wire 133a fixed to the second link B located at the most end of the bending part 130 pulls the second link B in the first direction a, and one end of the second link B is tilted towards the first direction a.

Since adjacent links are in rolling contact with each other, when one end of the second link B is tilted toward the first direction a, one end of the first link A in rolling contact with the second link B is also tilted.

When one end of the first link A is tilted, one end of the other link 131 in rolling contact with the first link A is also tilted, and one ends of the plurality of links 131 are generally tilted toward the first direction a through the above-described processes.

When the second portion 133bb of the second wire 133b moves in the second direction b, and one ends of the plurality of links 131 are tilted toward the first direction a, the other ends of the plurality of links 131 are tilted toward the second direction b.

As one ends of the plurality of links 131 are tilted in the first direction a and the other ends of the plurality of links 131 are tilted in the second direction b, the bending part 130 is generally bent in the clockwise direction c.

The process in which the bending part 130 is bent in the clockwise direction c has been described above, but the same principle is also applied to the process in which the bending part 130 is bent in the counterclockwise direction. That is, when the driving plate 139 is rotated in the counterclockwise direction, the plurality of links 131 in rolling contact with each other are generally bent in the counterclockwise direction.

Figure 11:
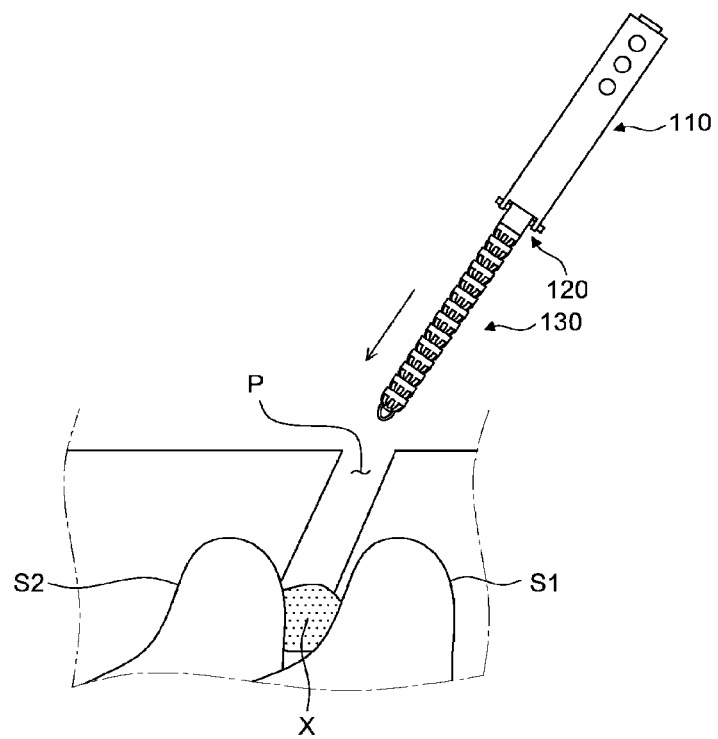
FIG. 11 is a diagram schematically illustrating a state before an apparatus for operation according to an exemplary embodiment of the present invention is inserted through a patient's incision hole.
Figure 12:
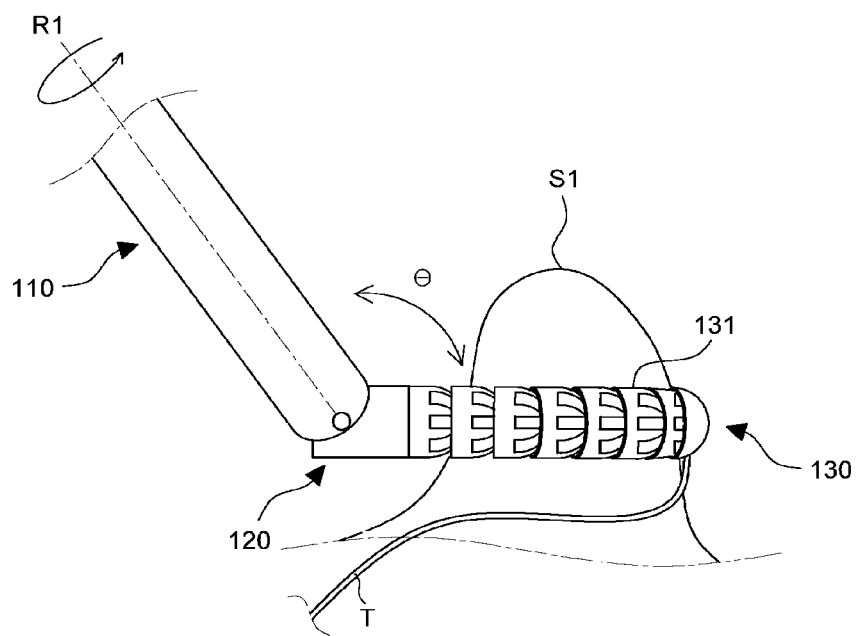
FIG. 12 is a diagram schematically illustrating a state in which the apparatus for operation according to an exemplary embodiment of the present invention wraps around a patient's spinous process.
Figure 13:
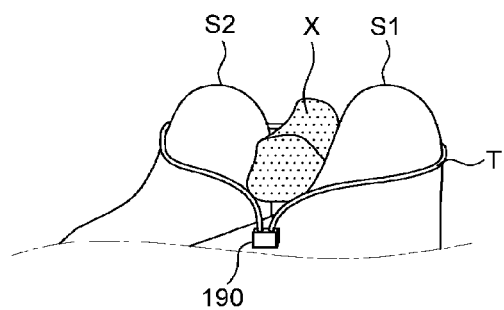
FIG. 13 is a diagram schematically illustrating a state in which a strap wraps around spinous processes.

FIG. 11 is a diagram schematically illustrating a state before an apparatus for operation according to an exemplary embodiment of the present invention is inserted through a patient's incision hole, FIG. 12 is a diagram schematically illustrating a state in which the apparatus for operation according to an exemplary embodiment of the present invention wraps around a patient's spinous process, and FIG. 13 is a diagram schematically illustrating a state in which a strap wraps around spinous processes.

Referring to FIGS. 11 to 13, the apparatus 100 for operation is configured to have a first shape in which the rotating part 120 and the bending part 130 are arranged substantially parallel to the rod 110 so that the rotating part 120 and the bending part 130 may be inserted into a body through an incision hole P, and a second shape in which the rotating part 120 is rotated with respect to the rod 110 or the bending part 130 is bent so that the bending part 130 wraps around spinous processes S1 and S2 in the body.

The apparatus 100 for operation may be fixed by a locking device (not illustrated) or the like in the first shape and the second shape.

In a state in which an interspinous spacer X is inserted between the spinous processes S1 and S2, the rotating part 120 and the bending part 130 may be inserted into the periphery of the patient's spinous processes S1 and S2 through the patient's incision hole P in the first shape disposed substantially parallel to the rod 110.

The rotating part 120 may be rotated to form an inclination angle θ to the rod 110. In this case, the bending part 130 may be rotated together with the rotating part 120.

In the state in which the rotating part 120 is rotated, the bending part 130 may be bent along the circumference of one S1 of the spinous processes.

In the state in which the strap T is inserted into the hole 140a, when the rotating part 120 is rotated with respect to the rod 110 and the bending part 130 is bent along the circumference of one S1 of the spinous processes, the strap T wraps around one S1 of the spinous processes. In the state in which the strap T wraps around one S1 of the spinous processes, when the rod 110 is rotated with respect to a rotation axis R1, the strap T inserted into the hole 140a of the blade 140 wraps around one S1 of the spinous processes while the bent bending part 130 is rotated around one S1 of the spinous processes.

In the state in which the rotating part 120 is not rotated with respect to the rod 110, by bending the bending part 130 and rotating the rod 110 about the rotation axis R1, the strap T may wrap around one S1 of the spinous processes. In addition, in the state of the rotation, it is possible to wrap around one of the spinous processes only by bending the bending part according to the surgical environment without the rotation about the rotation axis R1.

After the strap T wraps around one S1 of the spinous processes, the strap T may be separated from the apparatus 100 for operation.

After the apparatus 100 for operation is disposed on the periphery of the other S2 of the spinous processes, the strap T is inserted into the hole 140a, in the state in which the strap T is inserted into the hole 140a, the rotating part 120 is rotated with respect to the rod 110, and when the bending part 130 is bent along the circumference of the other S2 of the spinous processes, the strap T wraps around the other S2 of the spinous processes. In this state, when the rod 110 is rotated with respect to the rotation axis R1, the strap T inserted into the hole 140a of the protrusion wraps around the other S2 of the spinous processes while the bent bending part 130 is rotated around the other one S2 of the spinous processes.

In the state in which the rotating part 120 is not rotated with respect to the rod 110, by bending the bending part 130 and rotating the rod 110 about the rotating shaft R1, the strap T may wrap around the other S2 of the spinous processes. In addition, in the state of the rotation, it is possible to wrap around the other of the spinous processes only by bending the bending part according to the surgical environment without the rotation about the rotation axis R1.

After the interspinous spacer X is inserted between the spinous processes S1 and S2, in the state in which the strap T wraps around the spinous processes S1 and S2, one end of the strap T and the other end of the strap T may be fixed to each other by a coupling member 190. The coupling member 190 may be, for example, a clip or a buckle.

The coupling member 190 is configured to apply the tension to both ends of the strap T to maintain the tensioned state of the strap T. Therefore, the interspinous spacer X is firmly fixed between the spinous processes S1 and S2, and thus, the phenomenon that the interspinous spacer X is separated between the spinous processes is prevented. In addition, the stability of the corresponding vertebral segment including the spinous processes S1 and S2 is greatly improved.

In the above, the structure in which the apparatus 100 for operation includes the structure including the rod 110, the rotating part 120, and the bending part 130 has been illustrated and described as an example, but is not limited thereto.

For example, the apparatus 100 for operation may have the structure including only the rod 110 and the bending part 130 without the rotating part 120. In this case, the bending part 130 is directly coupled to the rod 110, and by bending the bending part 130 and manipulating the rod 110, the strap T may wrap around the spinous processes.

Figure 14:
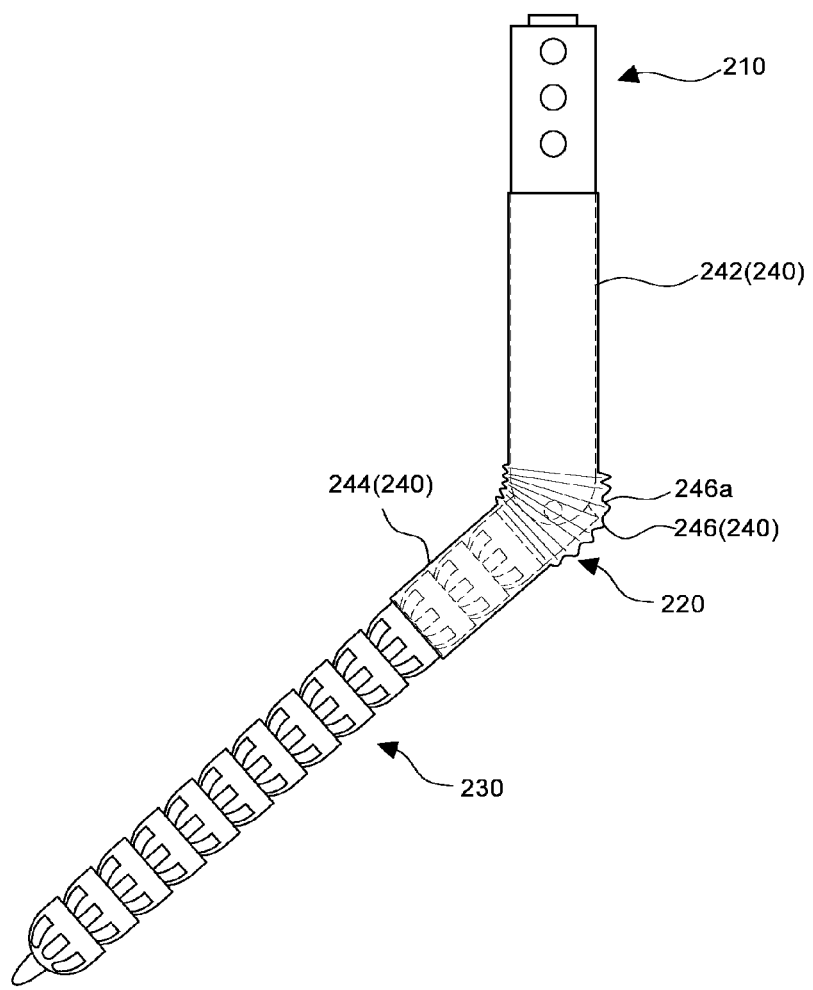
FIG. 14 is a diagram schematically illustrating an apparatus for operation according to another exemplary embodiment of the present invention.

FIG. 14 is a diagram schematically illustrating an apparatus for operation according to another exemplary embodiment of the present invention.

An apparatus 200 for operation according to another exemplary embodiment of the present invention includes a rod 210, a rotating part 220, a bending part 230, and a guide part 240. The rod 210, the rotating part 220, and the bending part 230 are the same as the apparatus 100 for operation according to an exemplary embodiment of the present invention described above, and therefore, a description thereof will be omitted.

The guide part 240 is provided in a shape of a hollow tube. The guide part 240 may be made of a hard and elastic material such as plastic or silicone, or may be made of a metal material and a joint part that needs to be rotated may be provided in the form of a mesh.

The rod 210, the rotating part 220, and the bending part 230 may be accommodated in the guide part 240.

The rod 210, the rotating part 220, and the bending part 230 may be in contact with the inner surface of the guide part 240 while the rod 210, the rotating part 220, and the bending part 230 are accommodated in the guide part 240.

The guide part 240 may include a first body 242 having both ends open, a second body 244 having both ends open, and a connection joint 246 connecting the first body 242 and the second body 244.

The connection joint 246 may include a wrinkle part 246a so that the second body 244 may be bent with respect to the first body 242.

The first body 242 and the second body 244 prevent the rod 210, the rotating part 220, and the bending part 230 accommodated therein from moving or rotating in an unwanted direction in a patient's body, or prevents the shape of the bending part 230 from being deformed, thereby enabling stable operation.

The guide part 240 may be inserted into the periphery of the patient's spinous processes S1 and S2 (see FIGS. 11 to 13) through the patient's incision hole P (see FIGS. 11 to 13) while the first body 242 and the second body 244 are substantially aligned side by side The rod 210, the rotating part 220, and the bending part 230 are guided to the periphery of the spinous processes S1 and S2 through the inside of the guide part 240 while the guide part 240 is inserted.

When the rotating part 220 is rotated or the bending part 230 is bent, an end of the bending part 230 may be disposed at a desired position while the second body 244 is bent with respect to the first body 242 by the wrinkle part 246a. Thereafter, the process of winding the strap T around the spinous processes S1 and S2 to fix the interspinous spacer X between the spinous processes S1 and S2 is the same as described above.

Although not shown, a modified exemplary embodiment of the apparatus 200 for operation according to another exemplary embodiment of the present invention described above is also applicable.

For example, the guide part 240 described above includes the first body 242, the wrinkle part 246a connected to the first body 242, and power transmission wires (not illustrated) disposed on an inner surface or an inner wall of the first body 242 and the wrinkle part 246a to rotate the wrinkle part 246a with respect to the first body 242 or fix the wrinkle part 246a in a state in which the wrinkle part 246a is rotated.

In addition, in response to the guide part as described above, the apparatus for operation may include only the bending part and a driving unit for driving the bending part without the rotating part.

In such a structure, the apparatus for operation passes through the guide part 240 and enters the periphery of the spinous processes S1 and S2 to perform functions such as muscle detachment, cauterization, and winding of the strap T after spacer insertion.

In addition, before the apparatus for operation is inserted by passing through the guide part 240, the guide part 240 may serve to guide the spacer X to the periphery of the spinous processes S1 and S2 through the inner side of the guide part 240.

Although exemplary embodiments of the present invention have been illustrated and described, the present invention is not limited to the above-described specific exemplary embodiment, but may be variously modified by those skilled in the art to which the present invention pertains without departing from the spirit and scope of the present invention as claimed in the claims. In addition, such modifications should also be understood to fall within the scope of the present invention.

What is claimed is:

1. An apparatus for operation configured to be inserted into a body through an incision hole, the apparatus for operation comprising:
    a rod having one end provided with a shaft; and
    a bending part that is bendable and rotatably connected to the shaft,
    wherein the bending part includes:
        a plurality of links being in rolling contact with each other;
        a plurality of wires connecting the plurality of links, the plurality of wires including a switching wire configured to bring the plurality of links into contact with each other or space the plurality of links apart from each other, other; and
        a blade configured to be coupled to a last link among the plurality of links and to receive a current via the switching wire.

2. The apparatus for operation of claim 1, wherein the plurality of wires further includes:
    at least one adjustment wire configured to bend the bending part while the plurality of links are spaced apart from each other.

3. The apparatus for operation of claim 2,
    wherein the bending part includes a driving plate disposed at one end of the bending part toward the rod,
    wherein the at least one adjustment wire includes a plurality of adjustment wires, and
    wherein a portion of the plurality of adjustment wires is configured to be wound around an outer circumferential surface of the driving plate.

4. The apparatus for operation of claim 2,
    wherein each of the plurality of links includes a link body, a convex portion formed on one side of the link body, and a concave portion formed on the other side of the link body and provided with a plurality of elastic bodies formed of an elastic material, and
    wherein each of the plurality of elastic bodies is provided in a spherical shape, and
    wherein the spherical shape of the elastic body is deformed when an external force is applied to the elastic body.

5. The apparatus for operation of claim 4, wherein
    each of the plurality of links includes a plurality of first through holes formed at an edge of the link body and a second through hole formed at a center of the link body,
    the at least one adjustment wire includes a plurality of adjustment wires, and
    each of the plurality of adjustment wires extends through one of the plurality of first through holes, and the switching wire extends through the second through hole.

6. The apparatus for operation of claim 5, wherein the plurality of first through holes are disposed on an outer side of the concave portion along a radial direction of the link body.

7. The apparatus for operation of claim 5, wherein the blade is inserted into the second through hole and connected to the switching wire.

8. The apparatus for operation of claim 1, wherein the apparatus for operation is configured to have
    a rotating part rotatably connected to the one end of the rod via the shaft,
    a first shape in which the rotating part and the bending part are arranged substantially parallel to the rod so that the rotating part and the bending part are inserted into the body through the incision hole, and
    a second shape in which the rotating part is rotated with respect to the rod or the bending part is bent so that the bending part wraps around a spinous process in the body.

9. The apparatus for operation of claim 1, wherein the bending part is configured so that at least a portion of the bending part is supplied with the current.

10. The apparatus for operation of claim 1, further comprising a guide part having a hollow body provided therein so that the bending part is inserted and guided, and a wrinkle part connected to one end of the hollow body and provided in a rotatable form.

11. An apparatus for operation configured to be inserted into a body through an incision hole, the apparatus for operation comprising:

a rod; and a bending part connected to the rod and bendable, wherein the bending part includes:

a plurality of links being in rolling contact with each other, each of the plurality of links including a link body, a convex portion formed on one side of the link body, and a concave portion formed on the other side of the link body and provided with a plurality of elastic bodies; and a plurality of wires connecting the plurality of links, the plurality of wires including:

a switching wire configured to bring the plurality of links into contact with each other or space the plurality of links apart from each other;

an adjustment wire configured to bend the bending part while the plurality of links are spaced apart from each other; and a blade configured to be coupled to a last link among the plurality of links and to receive a current.

* * * * *